(12) United States Patent
Ruetschi et al.

(10) Patent No.: US 10,966,802 B2
(45) Date of Patent: Apr. 6, 2021

(54) METHOD OF MANUFACTURING AN IMPLANT WITH TITANIUM-BASED THREE-DIMENSIONAL PRINTING MATERIAL

(71) Applicant: Ruetschi Technology AG, Muntelier (CH)

(72) Inventors: Christoph Ruetschi, Murten (CH); David Chenaux, Corcelles (CH); Bastien Boillat, Murist (CH)

(73) Assignee: Ruetschi Technology AG, Muntelier (CH)

( * ) Notice: Subject to any disclaimer, the term of this patent is extended or adjusted under 35 U.S.C. 154(b) by 0 days.

(21) Appl. No.: 16/489,508

(22) PCT Filed: Jun. 12, 2018

(86) PCT No.: PCT/IB2018/054244
§ 371 (c)(1),
(2) Date: Aug. 28, 2019

(87) PCT Pub. No.: WO2018/234928
PCT Pub. Date: Dec. 27, 2018

(65) Prior Publication Data
US 2020/0100874 A1 Apr. 2, 2020

(30) Foreign Application Priority Data
Jun. 20, 2017 (EP) .................................... 17177015

(51) Int. Cl.
*A61F 2/30* (2006.01)
*B33Y 10/00* (2015.01)
(Continued)

(52) U.S. Cl.
CPC ........ *A61C 8/0013* (2013.01); *A61F 2/30767* (2013.01); *A61C 2008/0046* (2013.01); (Continued)

(58) Field of Classification Search
None
See application file for complete search history.

(56) References Cited

U.S. PATENT DOCUMENTS 9,248,020 B2* 2/2016 Popoola ..................... A61F 2/28
2011/0143127 A1* 6/2011 Gupta ....................... A61L 27/54
428/336

(Continued)

FOREIGN PATENT DOCUMENTS

CN 101416906 A * 4/2009
CN 10361118 A 3/2014
(Continued)

OTHER PUBLICATIONS

International Search Report dated Oct. 29, 2018 for PCT/IB2018/054244.
(Continued)

*Primary Examiner* — Cachet I Proctor
(74) *Attorney, Agent, or Firm* — Andre Roland S.A.; Nikolaus Schibli (57) ABSTRACT

A method for manufacturing an implant including the steps of providing an implant element, the implant element made of a non-metallic material, depositing a thin layer of titanium-based material directly over an outer surface of the implant element, and forming a titanium-based structural body in direct contact with the thin layer by three-dimensional (3D) printing, the structural body being thicker than the thin layer of titanium-based material.

9 Claims, 6 Drawing Sheets

(51) Int. Cl.
  *A61C 8/00* (2006.01)
  *B33Y 80/00* (2015.01)
(52) U.S. Cl.
  CPC ............ *A61F 2002/30006* (2013.01); *A61F 2002/3092* (2013.01); *A61F 2002/3093* (2013.01); *A61F 2310/00023* (2013.01); *B33Y 10/00* (2014.12); *B33Y 80/00* (2014.12)

(56) References Cited

U.S. PATENT DOCUMENTS

| | | | | |
|---|---|---|---|---|
| 2016/0015483 A1* | 1/2016 | Kumar | ............... | A61C 8/0075 606/301 |
| 2016/0030632 A1* | 2/2016 | Schleicher | ............ | A61L 27/045 428/660 |
| 2016/0184103 A1* | 6/2016 | Fonte | ................ | A61L 27/56 623/23.5 |
| 2016/0331467 A1* | 11/2016 | Slamin | ................ | A61F 2/30756 |
| 2017/0348107 A1* | 12/2017 | Lee | ................ | A61F 2/30767 |
| 2018/0280143 A1* | 10/2018 | Gorhe | ................ | C25D 11/026 |

FOREIGN PATENT DOCUMENTS

| | | | |
|---|---|---|---|
| EP | 2332589 A2 | 6/2011 | |
| GB | 2477010 A | 7/2011 | |
| WO | WO 2012/068239 | 5/2012 | |

OTHER PUBLICATIONS

Written Opinion dated Oct. 29, 2018 for PCT/IB2018/054244.
EPO Notification 93(4) EPC of EP 17177015.9 dated Mar. 25, 2020.

\* cited by examiner

FIG.6

METHOD OF MANUFACTURING AN IMPLANT WITH TITANIUM-BASED THREE-DIMENSIONAL PRINTING MATERIAL

CROSS REFERENCE TO RELATED APPLICATIONS

The present patent application is a United States national stage application of International patent application PCT/IB2018/054244 filed on Jun. 12, 2018 designating the United States, and claims foreign priority to European Patent Application EP 17177015.9 that was filed on Jun. 20, 2017, the entire contents of both documents herewith incorporated by reference.

FIELD OF THE INVENTION

The present application is directed to the field of manufacturing implants with 3D printing techniques having a titanium-based structural body for bone integration, and implant devices made by the method.

BACKGROUND

In the field of implants, there is an interest in manufacturing the implant as a non-metallic component, for example a ceramic or a polymer component. Specifically, in the field of dental implants, these non-metal implants can be preferred for esthetical purpose, for example when there are margins at the gum level, to avoid showing metallic surfaces and dark shades at the gums. Also, non-metallic implants can have superior mechanical properties in terms of durability and hardness, and surface qualities, for example corrosion resistance and E-modulus. However, it has been shown that for non-metallic based implants, ossointegration and bioactivity may be difficult and substantially inferior to titanium based implants. In light of these disadvantages of the background art, substantially improved implants are desired, to provide for excellent ossointegration and biocompatibility, but still taking advantage of novel non-metallic based materials for the parts of the implant.

SUMMARY

According to one aspect of the present invention, a method for manufacturing an implant is provided. Preferably, the method includes the steps of providing an implant element, the implant element made of a non-metallic material, and depositing a thin layer of titanium-based material directly over an outer surface of the implant element. Moreover, the method further preferably includes a step of forming a titanium-based structural body in direct contact with the thin layer by three-dimensional (3D) printing, the structural body being thicker than the thin layer of titanium-based material.

According to another aspect of the present invention, an implant device is provided. The implant device includes a non-metallic implant body, and a thin layer of titanium-based material in direct contact with over an outer surface of the implant body. Moreover, the implant device preferably includes a porous titanium-based structural body in direct contact with the thin layer, the structural body being thicker than the thin layer of titanium-based material, wherein the titanium based structural body includes functional elements for ossointegration.

According to still another aspect of the present invention, a method for designing an implant for a target bone is provided. Preferably, the method includes the steps of imaging the target bone at areas where the implant will be in contact with the target bone to obtain bone density information, and analyzing the bone density information to determine a first area with a first bone structure and a second area with a second bone structure, the first and second areas to be in contact with the implant, and determining first and second structural features of the first and second bone structure, respectively. Moreover, the method further includes the steps of providing the implant having at least one of a titanium-based coating layer and a titanium-based outer surface, and three-dimensionally printing a first titanium-based structure and a second titanium based-structure at a first surface and a second surface of the implant, respectively, the first surface configured to be in contact with the first area of the bone, and the second surface configured to be in contact with the second area of the bone.

The above and other objects, features and advantages of the present invention and the manner of realizing them will become more apparent, and the invention itself will best be understood from a study of the following description with reference to the attached drawings showing some preferred embodiments of the invention.

BRIEF DESCRIPTION OF THE SEVERAL VIEWS OF THE DRAWINGS

The accompanying drawings, which are incorporated herein and constitute part of this specification, illustrate the presently preferred embodiments of the invention, and together with the general description given above and the detailed description given below, serve to explain features of the invention.

Herein, identical reference numerals are used, where possible, to designate identical elements that are common to the figures. Also, the images are simplified for illustration purposes and may not be depicted to scale.

DETAILED DESCRIPTION OF THE PREFERRED EMBODIMENTS

A first aspect of the method and implant device is shown with different frontal views as shown in FIGS. 1A to 1E, showing an implant 100, in the example shown a dental implant. Dental implant 100 includes a crown 50, an abutment 70, a screw 60, a non-metallic implant body or fixture 10, a thin interface layer 20 made of a titanium-based material and a structural body 30, both layer 20 and structural body 30 made of a titanium-based material, for example but not limited to a titanium alloys, titanium nitride (TiN). Titanium-based materials have shown to have very good characteristics for long-lasting and fast ossointegration, and structural body 30 is configured to have functional surfaces and volumes to facilitate this integration together with the titanium-based material. The non-metallic implant body 10 can be made of, but is not limited to, carbon, alumina, or zirconia ($ZrO_2$, $ZrO_2$ and $Y_2O_3$), or a combination thereof. In another variant, the implant body or fixture 10 can be made of a polymer, for example polyether ether ketone (PEEK). PEEK is often use having a E-modulus that is similar to the one of bone. Non-metallic implant body 10 has a flat interface surface 13 that is planar, interface surface 13 used for interconnection with titanium-based thin interface layer 20, see FIG. 1B. Surface 13 can be processed or otherwise treated to improve adhesion with titanium-based thin interface layer 20. Moreover, titanium-based thin interface layer 20 has an interface surface 25 for interconnection with titanium-based structural body 30, see FIG. 1C. Structural body 30 is made to be functional for integration to a bone, and can include an interface area 36 that is substantially solid, a body area 32 being structured for facilitated ossointegration, for example forming a porous, hollow, or trabecular structure, and a thread 34, the thread 34 also porous or made of trabecular structure. Also, it is possible that structural body 30 further includes specific cavities, porosities, or pockets for containing an ossointegration or mineralization agent. In a variant, it is possible that the entire structural body 30 is solid, and only an outer surface of solid body has a specific structure for functional integration with a bone.

Figure 1A:
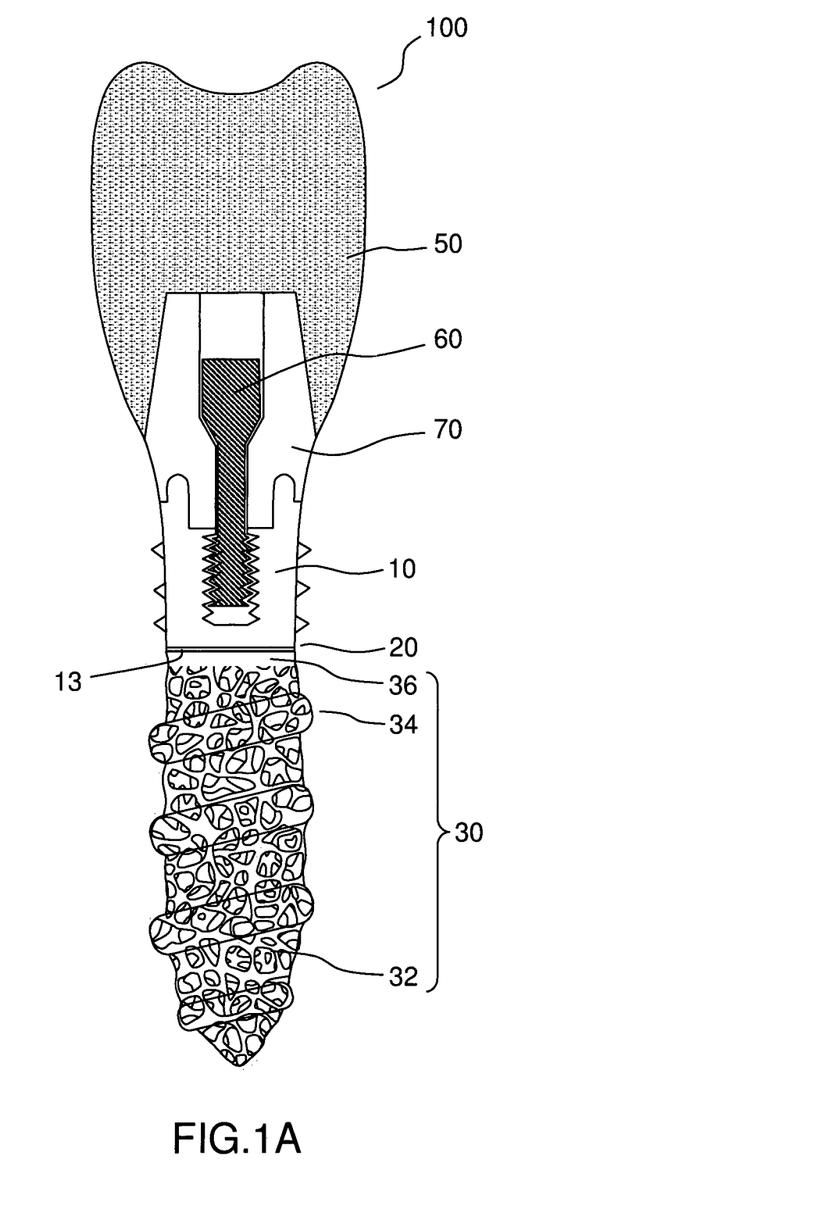
FIGS. 1A, 1B, 1C, 1D, and 1E schematically and exemplarily show different stages of non-metallic implant 100 when being manufactured by the method, according to one aspect of the present invention, with the example of a dental implant 100, with FIG. 1D showing a deposition apparatus, and FIG. 1E showing a 3D printing apparatus.
Figure 1B:
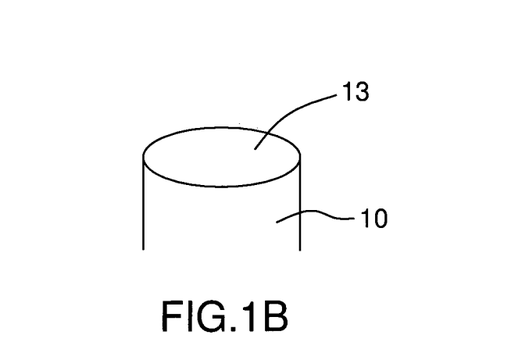
Figure 1C:
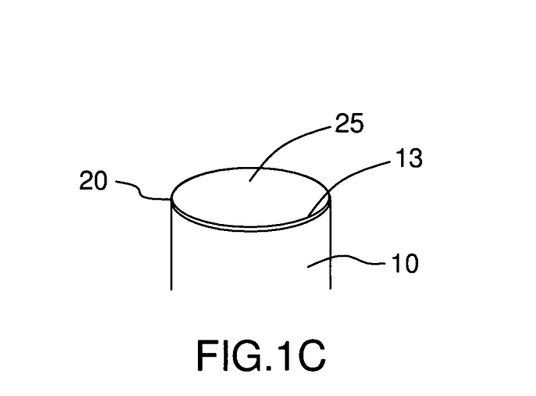
Figure 1D:
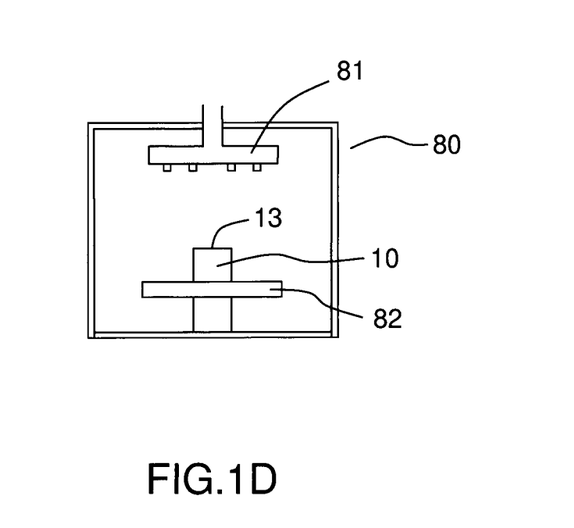

Regarding the method for manufacturing implant 100, the upper surface of non-metallic implant body 10 is coated with titanium-based thin interface layer 20. Thin interface layer 20 is formed on body 10 and serves as an adhesion layer to build up a larger structural body 30 made from the same or substantially the same material as the titanium-based interface layer 20. This allows to substantially improve adhesion between the non-metallic implant body 10 and titanium-based structural body 30, being a functional body for providing ossointegration with a bone of a patient. This process can include, but is not limited to a physical vapor deposition (PVD) process, a chemical vapor deposition (CVD) process, a diffusion coating process, titanium plasma spray (TPS). As schematically shown in FIG. 1D, non-metallic implant body 10 can be prepared and placed into a deposition chamber 80 having a shower head 81 and a chuck 82, and thereafter can be coated with titanium-based interface layer or film 20. Preferably, titanium-based layer 20 can have a thickness of less than 1 mm, more preferably the thickness can be in a range between 1 µm and 500 µm. Titanium-based thin layer 20 is formed to have an upper surface 25 that is substantially planar or flat, serving as a basis to build up a three-dimensionally (3D) printed titanium-based layer 20, as explained below.

Figure 5:
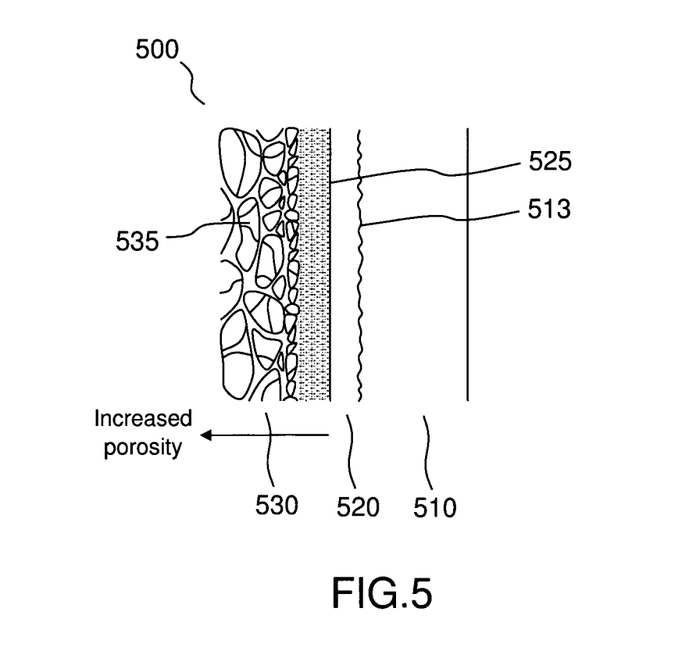
FIG. 5 schematically shows a cross-sectional view of an implant device 500, according to still another aspect of the present invention.

As an additional optional step, before forming titanium-based layer 20, surface 13 of implant body 10 can be prepared or treated for improved adhesion with titanium-based layer 20. For example, surface 13 can be treated to facilitate diffusion of titanium into non-metallic implant body 10, can be etched to create a microscopically or nanoscopically roughened surface area on implant body 10, while overall appearance of surface 13 is still planar. See for example in FIG. 5, showing roughened surface 513. As another example, surface 13 can be processed by a using plasma cleaner to improve surface adhesion, thereby creating a nanoscale roughness and removing contaminants. It is also possible that surface 13 is created by machining an upper surface of implant body 10, to make sure that the surface is planar, before performing a cleaning or adhesion improving step.

Figure 1E:
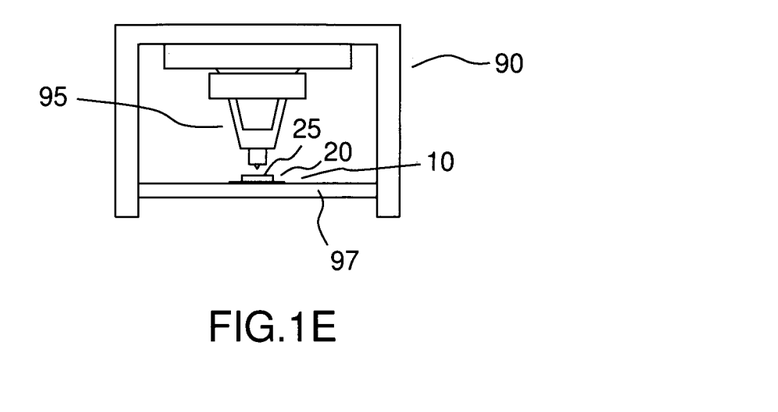

Next, non-metallic implant body 10 together with titanium-based thin layer 20 can be placed into a 3D titanium-based printing machine 90 as schematically shown in FIG. 1E, for forming titanium-based structural body 30 on top of surface 25 of titanium-based thin layer 20. Implant body 10 is thereby placed and secured to a fixation plate 97 so that a 3D printing head 95 can 3D print a titanium-based structure onto titanium-based thin layer 20, to form a functional body 30 for ossointegration. Preferably, the titanium-based material used for the thin layer 20 and body 30 is the same. When affixing implant body 10 to fixation plate 97, it is ascertained that upper surface 25 of titanium-based thin layer 20 is arranged to be parallel to an X and Y motion axis of the 3D printing head. The titanium-based printing can be done by laser sintering or e-beam sintering, for example direct metal laser sintering (DMLS)

As a 3D printing technique is used, titanium-based structural body 30 can be formed having very complex shapes, for example but not limited to 3D printing of a porous or trabecular body structure 32, the 3D printing of a thread 34 for the implant, 3D printing of an solid interface area 36 that gradually transitions into a porous or trabecular body structure 32. Also, specific features can be printed for containing and distributing bone agents for improved mineralization and ossointegration, for example interior channels and cavities inside body 30. Also, as further discussed below, specific features can be printed for body 30 to match a specific bone structure at the target bone. Body 30 is substantially larger or thicker than thin layer 20, and can be in the range from 1 mm to several centimeters. Body 30 can be made of a combination of different complex structures, for example but not limited to a trabecular structure, fibrous structure, spherical bead structure, asymmetrical powder structure, irregular particle coating structure, a chaotic structure, or a combination thereof.

This 3D printing technique for making the structural body 30 combined with the provision of a thin adhesion layer 20 allows to create structures for implants that have are impossible with traditional manufacturing and fabrication methods, offers new design possibilities to create patient-specific implants for a specific existing bone structure of a target bone, and the ability to create implants quickly and at a much lower cost.

As an additional optional step, after forming titanium-based thin layer 20 on surface 13 of non-metallic implant 10, titanium-based thin layer 20 can be cleaned or processed for facilitating adhesion and interconnection of the 3D printed titanium-based structural body 30 with thin layer 20, for example to provide for a defined surface roughness and or surface homogeneity. This can be done by a polishing step, chemical etching, etc.

Figures 2A, 2B, 2C:
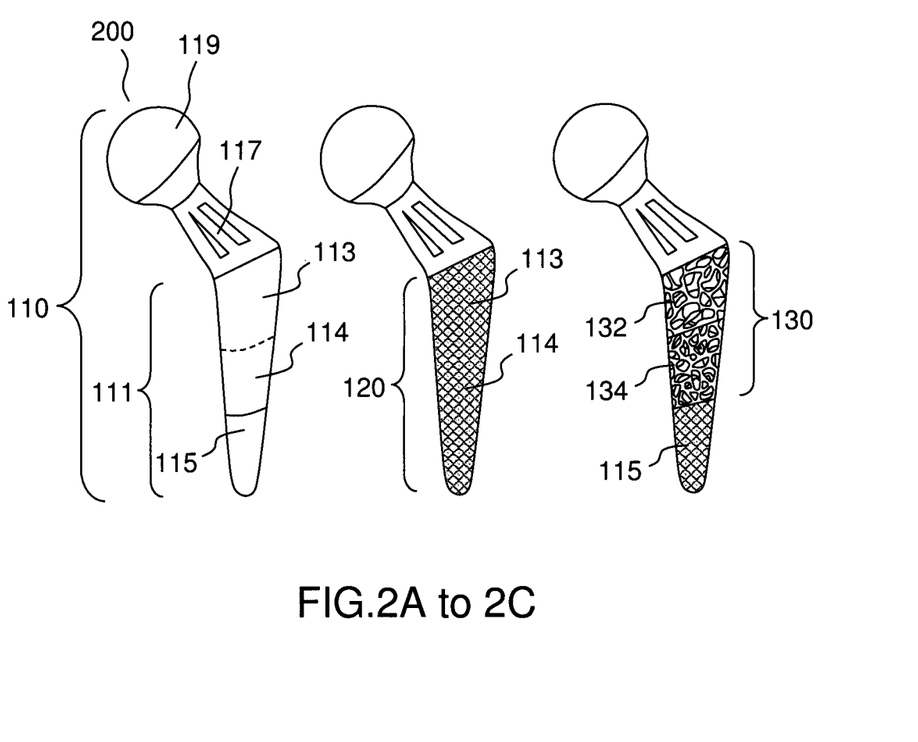
FIGS. 2A, 2B, 2C, and 2D schematically and exemplarily show different stages of non-metallic implant 200 when being manufactured by the method, according to another aspect of the present invention, with the example of a hip implant 200, with FIG. 2D schematically showing a multi-axis robot equipped with a 3D printing head.

Another aspect of the method and implant device is shown with different frontal views as shown in FIGS. 2A to 2C. First, as shown in FIG. 2A, a non-metallic implant 200 is provided, having a non-metallic body or fixture 110 that is not flat, for example but not limited to a dental implant, hip implant, maxillofacial implant and other head trauma implants, spine cage, disk implant. In FIG. 2A, a hip implant is shown for illustration purposes. The non-metallic implant body 110 includes a non-metallic femoral head 119, a femoral neck 117, a femoral stem 111, and the femoral stem 111 includes upper stem element 113, middle stem element 114, and lower stem element 115. In this variant, upper stem element 113 and middle stem element 114 are intended to form a solid connection to the target bone, being inner surfaces and structures of the upper femur.

Next, as shown in FIG. 2B, specific surfaces of the non-metallic implant 200 are subjected to a titanium-based deposition process, to form a thin layer, interface layer, or adhesion layer 120. In this deposition process, a thin layer of titanium-based material is deposited over a functional surface of non-metallic implant 200, the surface to be covered or coated being the surface of implant 200 that later needs to fuse with a target bone or bone structures. In the variant shown, an entire surface of stem 111 is determined to be the surface to be covered, and is coated by the deposition process, to form a thin titanium-based coating layer or film 120. Thin layer 120 is formed as a base or interface layer to build up a much larger structural body 130, that includes a porous structure made of titanium-based material, with the goal to provide for excellent mechanical connection and adhesion between non-metallic implant 200 and structural body 130, which includes adhesion, structural integrity, and structural continuity between thin layer 120 and structural body 130.

Figure 2D:
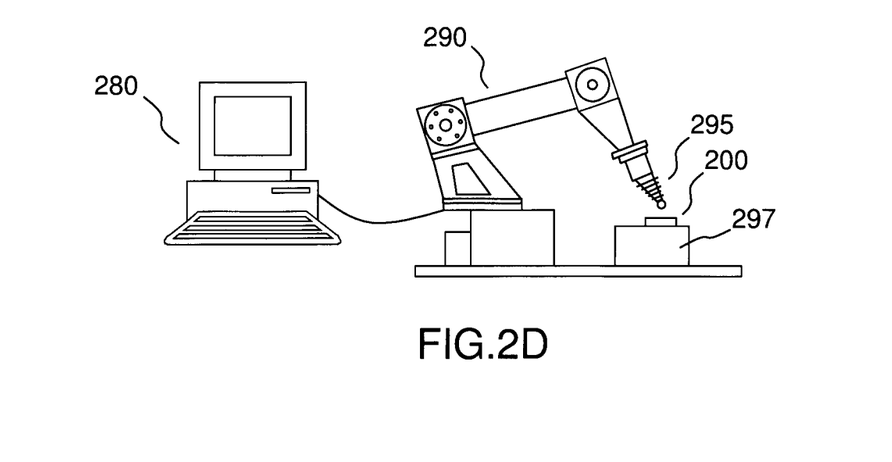

Next, as shown in FIG. 2C, structural body 130 made of a titanium-based material is formed on at least some portions of the surface of thin layer, interface layer, or adhesion layer 120, by a 3D printing process. In this 3D printing process, as the surface area 111 is not flat, unlike surface 13 shown in FIGS. 1A and 1B, such that the 3D printing process is carried out with a 3D printing head 295 that is mounted to a multi-axis high-precision robot 290, for example a six-axis high-precision industrial robot system, connected to a computer controller 280 that is configured to control the 3D printing operation of robot 290, such robot schematically shown in FIG. 2D. An exact position of implant 200 and surface geometry of surface area of stem 111 need to be known and stored in computer controller 280, so that the 3D printing can be carried out with sufficient precision. For example, a computer-aided design (CAD) model of implant 200 can be provided to computer controller 280, including an exact position and orientation of implant 200 on base 297.

In the variant shown, two surface areas of stem 111 are coated differently by 3D printing with a titanium-based material, being a first surface of upper stem element 113 and a second surface of middle stem element 114, both currently covered or coated with thin layer 120. Upper stem element 113 is covered by 3D printing with a first titanium-based structure body 132 having a first type of structural features, and middle stem element 114 is covered by 3D printing with a second titanium-based structure body 134 having a second type of structural features. In a variant, it is also possible to cover any surface of adhesion layer 120 with a single structure layer having the same structural features. Regarding the different structural features of structure bodies 132, 134, in the example shown, first structure body 132 can be made with first structural features having a large granularity or porosity, for example a trabecular structure with an average size of the pores of a larger size, while second structure body 134 can be made with second structural features that are different, for example having comparatively smaller granularity or porosity, for example a trabecular structure with an average size of the pores being smaller than the first structure.

The structure body 130, including first and second structure bodies 132, 134 are formed by the 3D printing, is configured to facilitate ossointegration to a target bone structure, for example to a model bone or specific bone of the patient. Different trabecular structures can be made, or another type of porous structure, or a layer having a specific surface roughness that facilitates ossointegration. Also, openings, pores, or channels can be 3D printed to be used for holding bioactive particles and other material, and for distributing these particles with body 130 and bone to facilitate bone formation and integration.

With the method described above, target-bone specific 3D structures for further facilitating ossointergration and bone reformation can be made. For example, specific structure bodies 132, 134 of the 3D printed structure can be formed as a trabecular structure to match a trabecular structure of the target bone, at a specific location where the target bone and the implant will be connected, for example but not limited to a matching an average pore diameter, average density, of an area of the target bone that will be in contact with implant.

Figure 3:
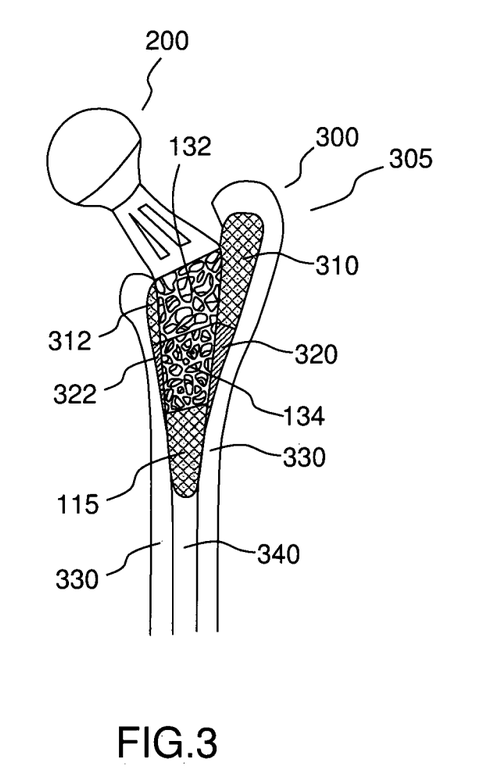
FIG. 3 schematically and exemplarily shows implant 200 that has been introduced and connected to a target bone 300, in the variant shown the upper femur.

FIG. 3 shows non-metallic implant 200 that has been introduced and connected to bone 300, in the variant shown a femur, being the target bone of the patient, in a hip replacement procedure. In the exemplary variant shown, provided for illustration purposes, the bone 300 has a femur head 305, marrow cavity 340, with the femur head 305 having three different bone structure areas, areas 310, 312 being areas of large porous trabeculae, areas 320, 322 being areas of small porous trabeculae, smaller than the porosity of the areas 310, 312, and areas 330 of osteon compact bone. Stem 111 of non-metallic implant 200 has been coated with different types of titanium-based structure by the method described above, so that the areas of stem 111 that face the different bone structure areas of bone 300 are attempted to be matched with different structural features that are necessary for improved ossointegration.

For example, different granularity, different porosity, surface roughness, different types of structures can be formed on respective different outer surface areas 113, 114, 115 of non-metallic implant 200, so that a structure of the corresponding bone structure areas of a target bone 300 can be matched or approximated. In the variant shown, in the final attachment position between implant 200 and bone 300, compact bone areas 330 are in contact with lower stem element 115 that is coated with a thin layer of titanium-based material, large porous areas 310, 312 of bone 300 are in contact with first titanium-based structure body 132 of implant 200, this layer having been printed by 3D printing, and small porous areas 320, 322 of bone 300 are in contact with second titanium-based structure body 134 of implant 200, this layer having also been printed by 3D printing.

Figure 4:
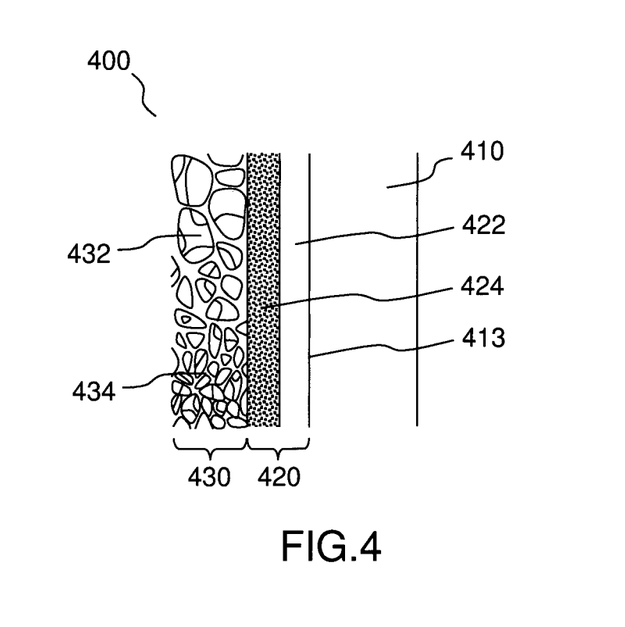
FIG. 4 schematically shows a cross-sectional view of an implant device 400 showing different layers and surfaces, according to one aspect of the present invention.

FIG. 4 shows a cross-sectional view of a surface of an implant device 400, according to another aspect of the present invention. Implant device 400 includes an implant body 410 made of a non-metallic material, for example a polymer or a ceramic, that is coated with a first, sold thin layer 422 of titanium based material, for example TiN, that has been provided by a deposition process as explained above. Next, a second, porous thin layer 424 is coated onto first, solid thin layer 422, also by a deposition process, made of the same titanium-based material. First and second layers 422, 424 form the thin layer, adhesion layer, or interface layer 420 that primarily serves to improve adhesion and structural integrity between structural body 430 and non-metallic implant body 410. Next, a 3D printed titanium-based structural body 430 is formed onto second, porous titanium-based thin layer 424. In the variant shown, the structure body 430 includes two different areas with a first structural body 432 having a first structure, and a second structural body 434 having a second structure, the first and second bodies 432, 434 having substantially the same thickness, but having different structure, for example first structural of body 432 having a trabecular structure having a larger porosity that the trabecular structure of the second structural body 434.

Thin layer 420 is usually made to be substantially thinner than the structural body 430. For example, while thin layer 420 is preferably below 1 mm, structural body 430 can be, but is not limited to a thickness range of 0.5 mm to 10 mm. Also, in the variant shown, the outer layer 424 of thin layer 420 is porous to increase adhesion to the 3D printed material of structural body 430. However, it is also possible that thin layer 420 is made of a single layer that has a gradually increasing porosity, from implant body 410 towards structural body 430.

FIG. 5 shows a cross-sectional view of a surface of an implant device 500, according to another aspect of the present invention. In this variant, a surface 513 of implant body 510 that will be coated is first processed to be roughened, cleaned, and treated to facilitate diffusion of a titanium-based material, or otherwise processed to increase adhesion between the later deposited titanium-based thin layer 520 and non-metallic implant body 510. For example, this can be done by a plasma cleaning process, to form nanoscale roughness. Next, a structure body 530 is 3D printed onto titanium-based material. In the variant shown, the structure layer 530 has an increased porosity towards an outer surface or structure 535 facing away from roughened surface 525, for example by successively increasing an average pore size in that direction. The deposited thin layer 520 is shown to be made of solid titanium-based material, and thereafter shows increased porosity towards the structural body 530. This allows to transition from a strong adhesion between thin layer 520 and structural body 530, to switch to a structure that improves and facilitates ossointegration at an outer surface or outer structure 535. It could also provide for a continuous mechanical transition from the thin layer 520 and the structure body 530, such that the porosity gradually increases from zero to a desired value, to avoid any abrupt changes in porosity that could weaken a bond or connection between thin layer 520 and structure body 530.

Figure 6:
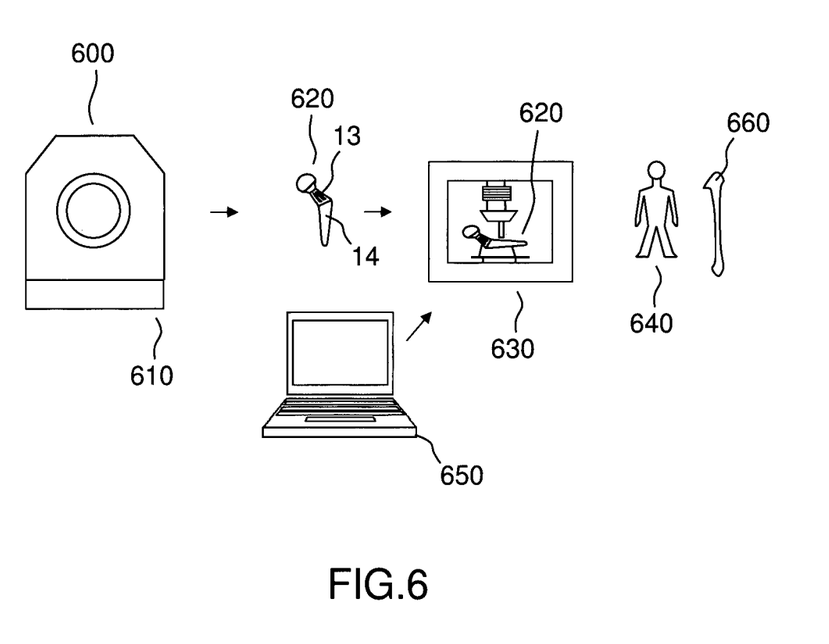
FIG. 6 schematically shows a manufacturing method 600 for manufacturing an implant device 620 specific for a target bone of a patient, according to yet another aspect of the present invention.

FIG. 6 shows an exemplary method 600 for manufacturing an implant that is specifically manufactured for a target bone of a specific patient. With the final structural arrangement between implant 620 and bone 660 being known, it is possible to create specific coatings, including thin layer 20 and structure body 30 of implant 620, to be matched or otherwise adapted to fit structure areas of a specific bone 660 of patient 640, this bone being the target for the implant. Thereby, it is possible to make implants 620 specific to a target bone 660 of a patient 640, to 3D print different types of titanium-based structures onto implant 620, depending on the existing bone structure. The method uses an imaging device 610 to first determine bone structures that are present in the target bone 660 of patient 640. To determine these bone structures, a non-intrusive technique is used, for example high-resolution tomographic techniques, such as high-resolution magnetic resonance imaging (MRI) and computed tomography (CT), for example multi-slice spiral CT and clinical micro-CT. The results of imaging device 610, for example 2D or 3D images that represent bone structure and density, can be analyzed by a computer 650 the determine different areas in the target bone, for example three-dimensional architecture of trabecular or other types of bone, at areas where target bone 660 and implant will interface.

Next, implant 620 can be provided with a 3D printed structure on top of thin layer 20, with structure body 30 that will be made to specifically match the different areas of bone structure in the target bone 660, at areas where implant 620 will interface with bone 660. For example, areas of different trabecular structure density in target bone 660 can be identified, and thereafter, a matching structure body 30 with different structural features 13, 14, can be 3D printed onto implant 620, with 3D printing device 620. For example, as shown in FIG. 3, two different bone areas may have been identified by computer 650, being a first bone area 310, 312 has a first range of bone density, and a second bone area 320, 322 that has a second range of bone density, the first and second range being different. Consequently, first and second structure bodies 32, 34 have been 3D printed with a titanium based material to match these density ranges, for the specific areas. This allows to take advantage of another feature of the titanium-based 3D printing, to make a customized structure body 30 onto implant 620. Preferably, implant 620 has previously been coated with thin or interface layer 20, and thereby, the 3D printing can be done upon determination of the structural features that need to be printed onto interface layer 20.

The above presented manufacturing method and resulting implant device shows substantial benefits over the background art. First, this manufacturing method allows to combine the advantages of a non-metallic based implant, in terms of strength, specific stiffness and elasticity, durability, and environmental resistance, with the biocompatibility, bioactivity, and ossointegration of titanium-based implants. For example, while a specific mechanical property can be preserved, for example a matching elastic modulus or stiffness with the bone, the advantages of titanium-based ossointergration can be added, and specifically structurally matched for the target bone. In addition, it is possible to reduce a time between the analysis of a bone structure and the insertion of a patient-specific implant, by using a 3D printing technique to manufacture the titanium-based parts of the implant that will interface or fusion with the bone. In addition, the use of a 3D printing technique allows to create complex titanium-based structures on a non-metal based implant, that may not be possible with other types of manufacturing techniques, for example the creation of trabecular structures having a chaotic or random arrangement of the beams, struts, or rods. Also, the titanium-based structure can be manufactured specific to a chosen target bone for the patient, to maximize the fusion effects with the bone. With a normal deposition process of a titanium-based material onto a non-metallic implant, it is not possible to create relatively thick layers, and also it is not possible to create certain functional structures that allow for enhanced ossointegration, for example a trabecular structure.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A method for manufacturing an implant comprising the steps of:
providing an implant element, the implant element made of a non-metallic material;
depositing a thin layer of titanium-based material directly over an outer surface of the implant element, the step of depositing including a first depositing process to form a first thin layer of solid material, and a second deposition process to for a second thin layer of porous material; and
forming a titanium-based structural body in direct contact with the thin layer by three-dimensional (3D) printing, the structural body being thicker than the thin layer of titanium-based material.

2. The method of claim 1, wherein the structural body is porous structure configured to facilitate a fusion with a bone.

3. The method of claim 2, wherein the porous structure includes at least one of a trabecular structure, fibrous structure, spherical bead structure, asymmetrical powder structure, irregular particle coating structure, chaotic structure.

4. The method of claim 1, wherein the step of depositing includes a physical vapor deposition (PVD) process, a chemical vapor deposition (CVD) process, a diffusion coating process, titanium plasma spray (TPS).

5. The method of claim 1, further comprising the step of:
cleaning and roughening the outer surface of the implant element.

6. The method of claim 1, wherein the step of forming the structure layer creates a inhomogoenous structure that matches a bone structure of a target bone.

7. A method for designing an implant for a target bone comprising the steps of:
imaging the target bone at areas where the implant will be in contact with the target bone to obtain bone density information;
analyzing the bone density information to determine a first area with a first bone structure and a second area with a second bone structure, the first and second areas to be in contact with the implant, and determining first and second structural features of the first and second bone structure, respectively;
providing the implant having at least one of a titanium-based coating layer and a titanium-based outer surface;
three-dimensionally printing a first titanium-based structure and a second titanium based-structure at a first surface and a second surface of the implant, respectively, the first surface configured to be in contact with the first area of the bone, and the second surface configured to be in contact with the second area of the bone.

8. The method according to claim 7, wherein the step of imaging is performed by at least one of an x-ray device, a magnetic resonance imaging device, a computer tomography device.

9. The method according to claim 7, wherein the step of imaging provides for information on bone densiometry of the target bone.

* * * * *